(12) United States Patent
Lim et al.

(10) Patent No.: US 9,011,335 B2
(45) Date of Patent: *Apr. 21, 2015

(54) ULTRASONIC DIAGNOSTIC APPARATUS AND CONTROL METHOD THEREOF

(71) Applicant: Samsung Electronics Co., Ltd., Suwon (KR)

(72) Inventors: Chai Eun Lim, Seoul (KR); Kang Sik Kim, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/043,459

(22) Filed: Oct. 1, 2013

(65) Prior Publication Data

US 2014/0031695 A1     Jan. 30, 2014

Related U.S. Application Data

(63) Continuation of application No. 13/205,972, filed on Aug. 9, 2011, now Pat. No. 8,568,321.

(30) Foreign Application Priority Data

Aug. 9, 2010 (KR) .................. 10-2010-0076649

(51) Int. Cl.
    *A61B 8/00*     (2006.01)
    *A61B 8/08*     (2006.01)
    *G10K 11/34*     (2006.01)
    *G01S 7/00*     (2006.01)

(52) U.S. Cl.
    CPC .............. *A61B 8/5207* (2013.01); *G01S 7/003* (2013.01); *G10K 11/341* (2013.01)

(58) Field of Classification Search
    USPC .......................... 600/437–469; 382/128–132
    See application file for complete search history.

(56) References Cited

U.S. PATENT DOCUMENTS

| | | | |
|---|---|---|---|
| 6,595,921 B1 * | 7/2003 | Urbano et al. | 600/437 |
| 2004/0102700 A1 | 5/2004 | Asafusa et al. | |
| 2007/0232925 A1 | 10/2007 | Satoh | |
| 2008/0212887 A1 | 9/2008 | Gori et al. | |
| 2010/0331689 A1 * | 12/2010 | Wegener | 600/443 |
| 2011/0097006 A1 * | 4/2011 | Mansour | 382/251 |
| 2012/0157852 A1 * | 6/2012 | Wegener et al. | 600/454 |

FOREIGN PATENT DOCUMENTS

| | | |
|---|---|---|
| CN | 101064850 A | 10/2007 |
| JP | 2009000361 A | 1/2009 |

OTHER PUBLICATIONS

International Search Report Issued on Apr. 24, 2012, in corresponding Application No. PCT/KR2011/005736.
Communication, issued by State Intellectual Property Office of P.R. China, dated Jun. 30, 2014, in counterpart Chinese Application No. 201180046863.7.

\* cited by examiner

*Primary Examiner* — Sanjay Cattungal
(74) *Attorney, Agent, or Firm* — Sughrue Mion, PLLC

(57) ABSTRACT

An ultrasonic diagnostic apparatus includes a probe including a transducer which transmits an ultrasound signal to a target, receives the ultrasound signal reflected from the target, and transduces the received ultrasound signal into an analog signal; an A/D converter which converts the analog signal output by the probe into a digital signal; a compression unit which compresses the digital signal output from the A/D converter; and a host computer which decompresses the digital signal compressed by the compression unit and performs beamforming.

17 Claims, 6 Drawing Sheets

FIG. 5

|     |     | nn | nne |
|-----|-----|----|-----|
|     | nw  | n  | ne  |
| ww  | w   | ?  |     |

ONE IMAGE

ULTRASONIC DIAGNOSTIC APPARATUS AND CONTROL METHOD THEREOF

CROSS-REFERENCE TO RELATED APPLICATIONS

This application is a continuation of U.S. application Ser. No. 13/205,972, filed Aug. 9, 2011, which claims priority from Korean Patent Application No. 10-2010-0076649, filed Aug. 9, 2010 in the Korean Intellectual Property Office, the entire disclosures of which are incorporated herein by reference.

BACKGROUND

1. Field

Apparatuses and methods consistent with embodiments relate to an ultrasonic diagnostic apparatus to create a two or three-dimensional image of an internal shape of a target and a control method thereof.

2. Description of the Related Art

An ultrasonic diagnostic apparatus transmits ultrasound to a target to be tested and receives the ultrasound signal reflected from the target. The ultrasonic diagnostic apparatus converts the received ultrasound signal into an electrical image signal to display an internal state of the target. The ultrasound signal is transmitted and received through a probe. The probe includes a transducer to transduce an electrical signal into a transmitting ultrasound signal, and to transduce the ultrasound signal reflected from the target into an electrical image signal. A plurality of transducers arranged in various forms may be used to improve resolution.

Referring to FIG. 1, which shows an example of a probe including a plurality of transducers 10, ultrasound signals transmitted from the respective transducers 10 are set to be simultaneously focused upon a focus point located at a depth d. The distance between a center transducer Tc and the focus point is the shortest, and the distance between an end transducer Tn and the focus point is the longest. A related art ultrasonic diagnostic apparatus includes a transmission beamformer to generate a plurality of transmission signals in view of differences in the distances between the focus point and the respective transducers 10. The transmission beamformer generates a plurality of electrical transmission signals, i.e., transmission beams, based on a delay profile which takes into account the differences in the distances between the respective transducers and the focus point. The transmission beams are transmitted to the respective transducers 10. The transducers 10 transduce the transmission beams into ultrasound signals, which are transmitted to the focus point.

The times needed for the ultrasound signals reflected from the focus point to reach the respective transducers 10 are different. An ultrasound reflection signal directed to the center transducer Tc travels a distance r. On the other hand, an ultrasound signal reaching a transducer Tx distant from the center transducer Tc by a distance x has a time delay corresponding to a difference Δr in the distance between the transducers Tx and Tc and the focus point. The beamformer compensates for the delay in receiving the signals at the respective transducers based on the position of the center transducer Tc.

SUMMARY

Exemplary embodiments provide an ultrasonic diagnostic apparatus that performs a beamforming operation using software, and a control method thereof.

In accordance with an aspect of an exemplary embodiment, there is provided an ultrasonic diagnostic apparatus including a probe including at least one transducer to transmit an ultrasound signal to a target, receive an ultrasound signal reflected from the target, and transduce the received ultrasound signal into an analog signal, an analog-to-digital (A/D) converter to convert the analog signal output from the probe into a digital signal, a compression unit to compress the digital signal output from the A/D converter, and a host computer to decompress the digital signal compressed by the compression unit and to perform beamforming.

The compression unit may predict a target pixel of the digital signal from an ambient pixel to generate a prediction error signal, and code the prediction error signal to perform compression.

The compression unit may generate the prediction error signal by calculating the prediction error signal using horizontal (channel-direction) data, vertical (depth-direction) data, and vector-direction (time-direction) data of the digital signal.

The compression unit may generate the prediction error signal using the horizontal (channel-direction) data, the vertical (depth-direction) data, and the vector-direction (time-direction) data of the digital signal by applying a higher weight factor to the vertical direction and the vector-direction data than the horizontal data to generate a prediction signal and calculating a difference between a pixel value of the prediction signal and a pixel value of a real signal to generate the prediction error signal.

The compression unit may code the prediction error signal to perform compression by creating a compressed code word from a sequence of the prediction error signal and coding the compressed code word.

The compression unit may remove spatial redundancy, temporal redundancy and statistical redundancy from the digital signal to perform compression.

The host computer may perform beamforming to create a frame data signal, and perform digital signal processing on the frame data signal to create ultrasonic image data.

The host computer may convert the ultrasonic image data into image frame data having a scan line display format.

The ultrasonic diagnostic apparatus may further include a display unit to receive and display the image frame data.

In accordance with an aspect of another exemplary embodiment, there is provided a method of controlling an ultrasonic diagnostic apparatus, the method including compressing an ultrasound signal reflected from a target, and transmitting the compressed signal to a host computer which decompresses compressed signal and performs beaming forming.

Compressing the ultrasound signal may include predicting a target pixel of the ultrasound signal from an ambient pixel to generate a prediction error signal and coding the prediction error signal to perform compression.

Predicting the target pixel of the ultrasound signal from the ambient pixel to generate the prediction error signal may include generating the prediction error signal based on a horizontal variation, a vertical variation, and a time-direction variation of the ultrasound signal.

Generating the prediction error signal based on the horizontal variation, the vertical variation, and the time-direction variation of the ultrasound signal may include applying a higher weight factor to the vertical variation and the time-direction variation than the horizontal variation to calculate a prediction signal and determining a difference between a pixel value of the prediction signal and a pixel value of a real signal to generate the prediction error signal.

Coding the prediction error signal to perform compression may include creating a compressed code word from a sequence of the prediction error signal and coding the compressed code word.

The control method may further include removing spatial redundancy, temporal redundancy and statistical redundancy from the ultrasound signal to perform compression.

In accordance with an aspect of another exemplary embodiment, there is provided a method of controlling an ultrasonic diagnostic apparatus, the method including compressing an ultrasound signal reflected from a target, converting the ultrasound signal into a digital signal, predicting a target pixel of the digital signal from an ambient pixel to generate a prediction error signal, coding the prediction error signal to perform compression, and performing beamforming using a host computer when the compressed data is transmitted to the host computer.

Predicting the target pixel of the digital signal from the ambient pixel to calculate the prediction error signal may include calculating the prediction error signal based on horizontal (channel-direction) data, vertical (depth-direction) data, and vector-direction (time-direction) data of the digital signal.

Generating the prediction error signal using the horizontal (channel-direction) data, the vertical (depth-direction) data, and the vector-direction (time-direction) data of the digital signal may include applying a higher weight factor to the vertical direction and the vector-direction data than the horizontal data to generate a prediction signal and generating a difference between a pixel value of the prediction signal and a pixel value of a real signal.

Coding the prediction error signal to perform compression may include creating a compressed code word from a sequence of the prediction error signal to code the compressed code word and performing compression.

BRIEF DESCRIPTION OF THE DRAWINGS

The above and/or other aspects will become apparent and more readily appreciated from the following description of exemplary embodiments, taken in conjunction with the accompanying drawings of which:

FIG. 5 is a view illustrating a method of calculating a prediction error of an ultrasound signal using a CALIC prediction method, according to one exemplary embodiment.

DETAILED DESCRIPTION

Figure 1:
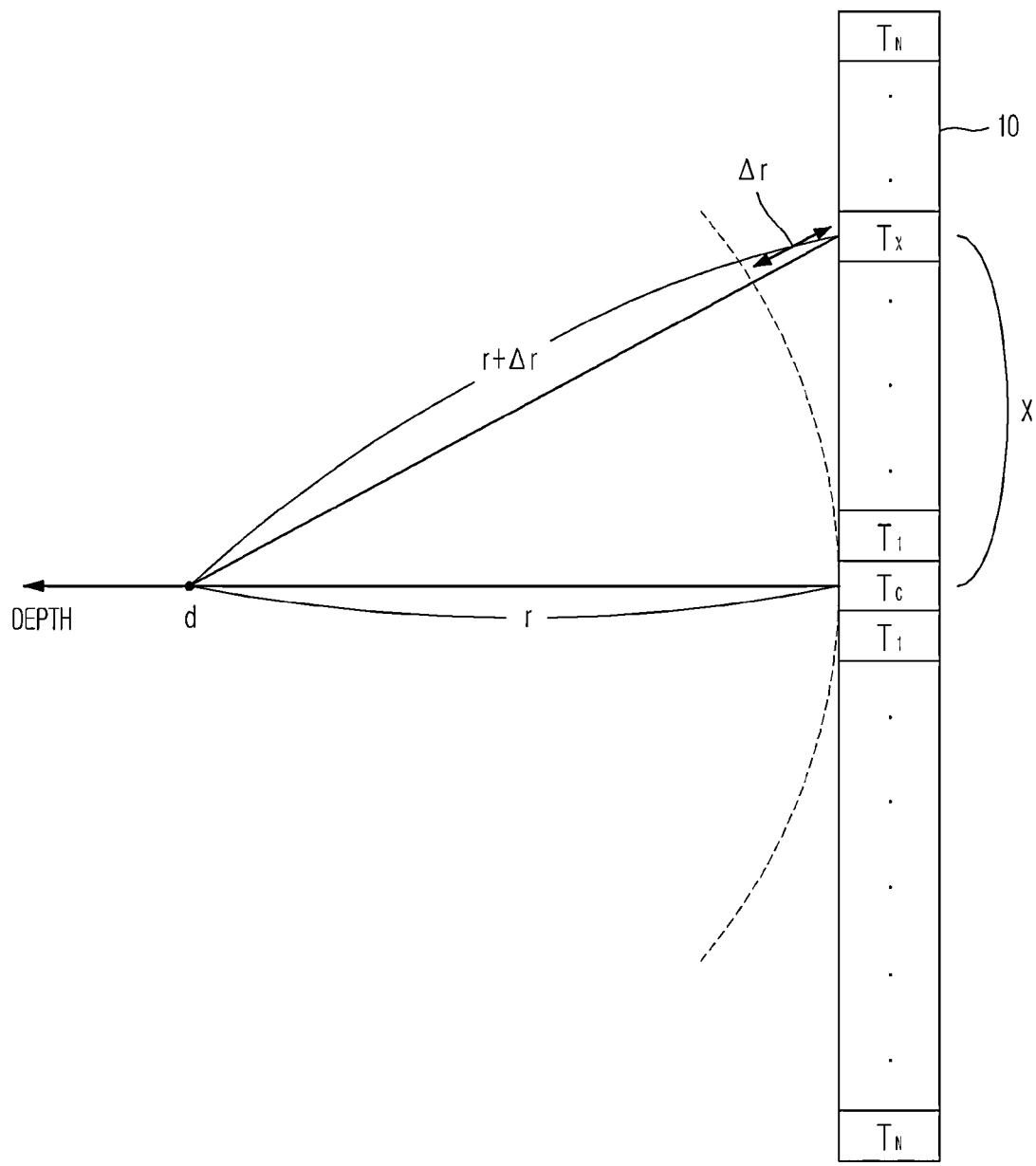
FIG. 1 is a schematic view illustrating an ultrasound signal transmission and reception focusing method using a transducer array.

Reference will now be made in detail to exemplary embodiments, examples of which are illustrated in the accompanying drawings, wherein like reference numerals refer to like elements throughout.

Figure 2:
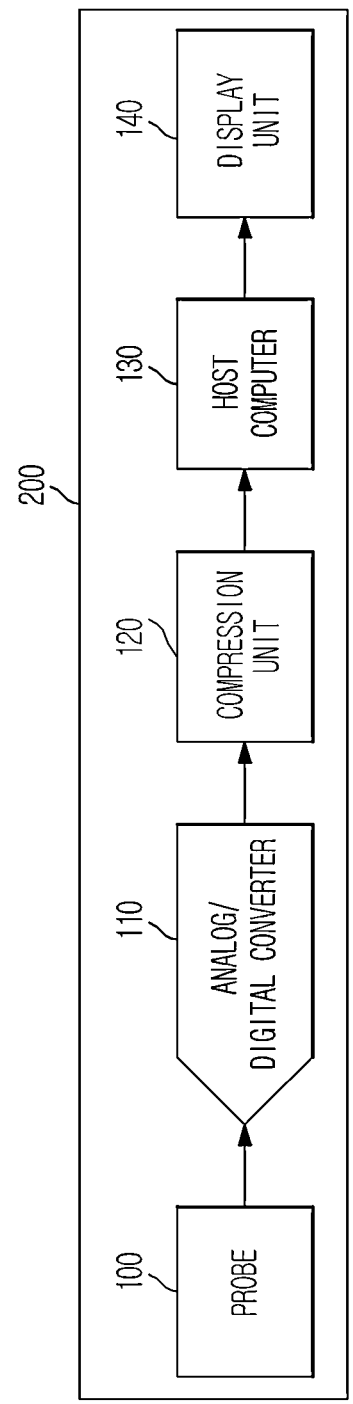
FIG. 2 is a functional block diagram of an ultrasonic diagnostic apparatus, according to an exemplary embodiment.

FIG. 2 is a function block diagram of an ultrasonic diagnostic apparatus 200 according to an exemplary embodiment.

The ultrasonic diagnostic apparatus 200 includes a probe 100, an analog-to-digital (A/D) converter 110, a compression unit 120, a host computer 130, and a display unit 140.

The probe 100 includes at least one transducer (not shown) to transduce an electrical signal into an ultrasound signal and transmit the ultrasound signal to a target. The at least one transducer may also receive the ultrasound signal reflected from the target and transduce the ultrasound signal into an electrical signal (analog signal). The analog signal output from the probe 100 has a center frequency related to properties of the transducer and tissues.

The A/D converter 110 converts the analog signal output from the probe 100 into a digital signal by sampling the analog signal at a fixed sampling rate of, for example, 60 MHz. The A/D converter 110 performs sampling at such a fixed sampling rate irrespective of the size of the center frequency of the analog signal. When the center frequency of the analog signal is low, therefore, a relatively large amount of digital signals is acquired. When the center frequency of the analog signal is high, on the other hand, a relatively small amount of digital signals is obtained. When the probe 100 includes a plurality of transducers, a plurality of A/D converters 110 corresponding to the respective transducers is provided.

The compression unit 120 compresses the digital signal output from the A/D converter 110. Upon reception of the digital signal output from the A/D converter 110, the compression unit 120 compresses the digital signal.

The compression unit 120 may use a lossless compression process to compress the digital signal. The lossless compression process compresses the digital signal such that when the compressed data is restored, the restored data completely coincide with data before compression.

The compression unit 120 may use context-based, adaptive, lossless image coding (CALIC), or Lossless JPEG from the Joint Photographic Experts Group (JPEG-LS) as the lossless compression technology.

The CALIC compression method is described in detail in X. Wu and N. Memon, "Context-based, adaptive, lossless image coding," IEEE Transactions on Communications, Vol. 45, No. 4, April 1997, pp. 437-444, the disclosure of which is incorporated herein.

The JPEG-LS compression method is described in detail, for example, in "Lossless and non-lossless coding of continuous tone still images," ISO/IEC JTC1/SC29 WG1 14495, the disclosure of which is incorporated herein.

The CALIC and JPEG-LS compression methods use differential pulse code modulation (DPCM). Each pixel of a picture is scanned every line and every row. DPCM predicts a target pixel from an ambient pixel to code a prediction error signal thereof. DPCM losslessly encodes original information.

That is, upon lossless compression, a prediction error signal is calculated based on a value of an ambient pixel around each pixel. An entropy encoder encodes the calculated prediction error signal of the pixel value, i.e., the difference between an effective value and the pixel value of the prediction signal. The lossless compression methods used in exemplary embodiments are not limited to CALIC and JPEG-LS. Other known lossless compression methods may be used. In addition, lossy compression methods may also be used. Since exemplary embodiments are applied to medical imaging, lossless compression methods may be primarily used. One of the lossless compression methods, CALIC, will be described in detail with reference to FIGS. 3 to 5.

The host computer 130 decodes the data transmitted from the compression unit 120 to decompress the data, and performs a beamforming operation using software to create frame data signals, which are raw data. Beamforming is a process in which some of the digital signals are processed at a rate corresponding to an integer multiple of the center frequency to form a reception beam. The host computer 130 converts the digital signals output from the compression unit 120 into a predetermined number of frame data signals.

The host computer 130 digital signal processes the frame data signals to form ultrasonic image data that express a B, C or D mode.

The host computer 130 converts the ultrasonic image data into a predetermined scan line display format, which is a data format used in the display unit 140. That is, the host computer 130 converts the ultrasonic image data signals into image frame data that is displayed in the display unit 140.

The host computer can be a processor unit. The processor unit can be a CPU, GPU and Computer.

The display unit 140 receives the image frame data to display an ultrasound image.

The communication of data of two of the probe 100, an A/D converter 110, a compression unit 120, host computer 130 and the display unit 140, may be performed using one of a cable and a wireless network.

Figure 3:
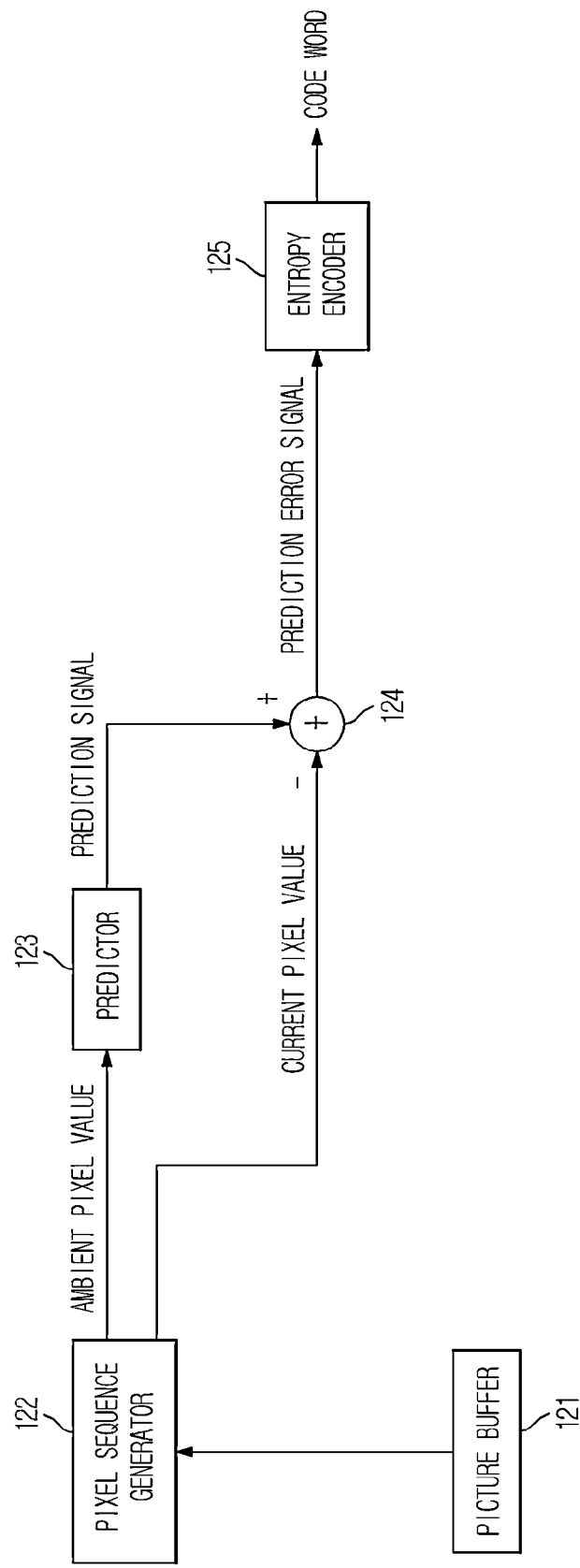
FIG. 3 is a detailed block diagram of a compression unit included in the ultrasonic diagnostic apparatus, according to an exemplary embodiment.
Figure 4:
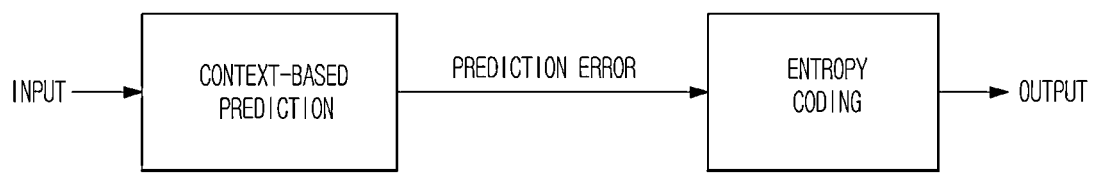
FIG. 4 is a block diagram illustrating a context-based, adaptive, lossless image coding (CALIC) compression method.

FIG. 3 is a detailed block diagram of the compression unit included in the ultrasonic diagnostic apparatus according to an exemplary embodiment, and FIG. 4 is a block diagram illustrating a context-based, adaptive, lossless image coding (CALIC) compression method.

The compression unit 120 includes a picture buffer 121, a pixel sequence generator 122, a predictor 123, an adder 124, and an entropy encoder 125.

The image buffer 121 accumulates a picture input from an external apparatus. The pixel sequence generator 122 scans the picture accumulated in the picture buffer 121 to extract an ambient pixel from a current pixel, i.e., a target pixel. For each pixel, the pixel sequence generator 122 supplies a pixel value of the current pixel to the adder 124 and also supplies a pixel value of the ambient pixel to the predictor 123.

The predictor 123 creates a prediction signal based on the pixel value of the ambient pixel supplied from the pixel sequence generator 122 and supplies the prediction signal to the adder 124. The adder 124 subtracts the prediction signal supplied from the predictor 123 from the pixel value of the current pixel supplied from the pixel sequence generator 122 to obtain a prediction error signal and supplies the prediction error signal to the entropy encoder 125.

The entropy encoder 125 creates and outputs a compressed code word from a sequence of the prediction error signal supplied from the adder 124.

The prediction error signal is coded into a prefix having a variable length and a suffix having a fixed length. The prefix having the variable length is a series of "0" bits following "1" bits. The sequence of the prediction error signal is partitioned into blocks. For each block, an optimum length of the suffix is decided first. The code word is transmitted before the code word is coupled to the prediction error signal of each block. The entropy encoder 125 is described in detail, for example, in R. Rice, "Lossless coding standards of space data systems," IEEE 1997, the disclosure of which is incorporated herein.

The above-described coding method is divided into prediction and entropy coding, as shown in FIG. 4. CALIC prediction will be described in detail with reference to FIG. 5.

CALIC entropy coding uses Huffman coding and arithmetic coding, which are conventional coding methods.

The Huffman coding is a form of entropy coding which is used in lossless compression. The Huffman coding is an algorithm using codes having different lengths according to the estimated probability of occurrence of specific data segments. Upon coding of different letters, Huffman coding does not use a fixed number of bits but uses statistical distribution. Therefore, Huffman coding is a coding method using a smaller number of bits with respect to a frequently appearing value and a larger number of bits with respect to an infrequently appearing value.

Arithmetic coding is a form of entropy coding which is used in lossless compression. Arithmetic coding estimates a probability of an input signal from a frequency of occurrence of the input signal. In other forms of entropy coding, each symbol is replaced with a code in a one-to-one correspondence. In arithmetic coding, on the other hand, an entire message is replaced with a single real number n.

The Huffman coding and the arithmetic coding are conventional technologies, and therefore, a detailed description thereof is not necessary.

Figure 5:
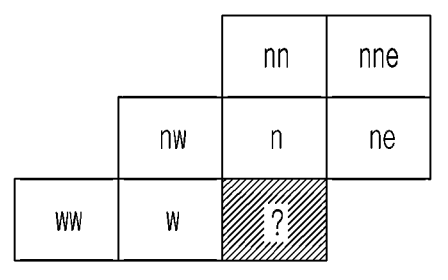

FIG. 5 is a view illustrating a method of calculating a prediction error of an ultrasound signal using a CALIC prediction method.

An ultrasound signal reflected from a target exhibits a spatial redundancy having similarity in axial and azimuth directions. Also, the ultrasound signal has a statistical redundancy in which a prediction error is increased in proportion to a horizontal variation or a channel-direction variation dh and a vertical variation or a depth-direction variation dv (see FIG. 6 in connection with the horizontal and vertical variations).

The CALIC compression method predicts a pixel value using gradient-adjusted prediction (GAP) to obtain a prediction error e, which is the difference between a predicted value $\hat{I}$ and a real value I. The horizontal variation dh, the vertical horizontal variation dv, the predicted value $\hat{I}$, and the real value I may be obtained using the following equation:

$$\hat{I}=GAP(\&dh,\&dv)$$

$$dh=\text{abs}(I(w)-I(ww))+\text{abs}(I(n)-I(nw))+\text{abs}(I(ne)-I(n))$$

$$dv=\text{abs}(I(w)-I(nw))+\text{abs}(I(n)-I(nn))+\text{abs}(I(ne)-I(nne))$$

$$e=I-\hat{I}$$

I(w) is a pixel value of a point located at w of FIG. 5, I(ne) is a pixel value of a point located at ne of FIG. 5, and abs( ) is an absolute value of a value in parentheses.

The ultrasound signal reflected from the target exhibits higher similarity in the axial direction than in the azimuth direction. Therefore, to obtain the prediction error, a higher weight factor is applied to the vertical variation or the depth-direction variation dv than to horizontal variation or a channel-direction variation dh.

Figure 6:
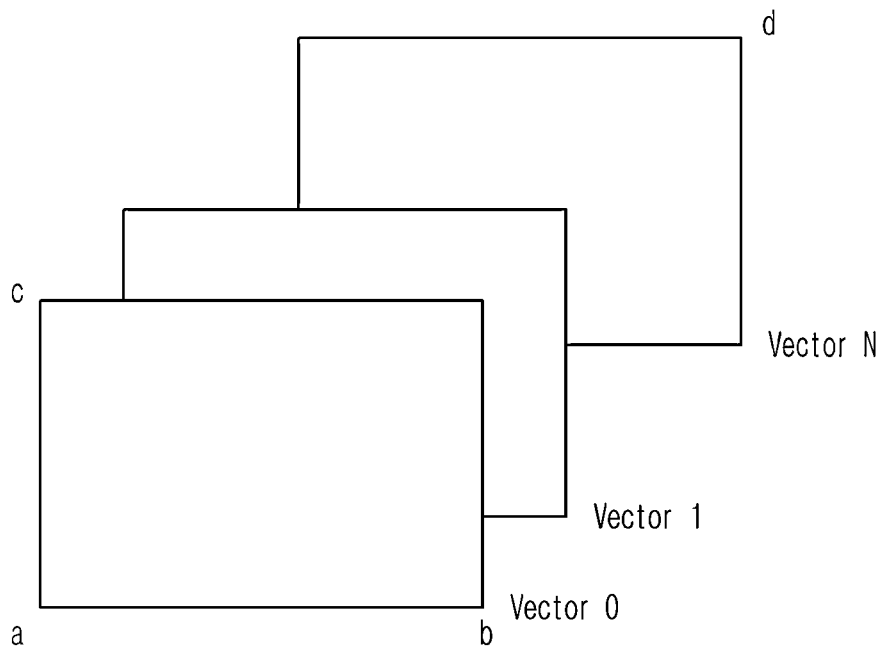
FIG. 6 is a schematic view illustrating a time-based arrangement of a plurality of vectors on an image acquired from an ultrasound signal, according to one exemplary embodiment.
Figure 6:
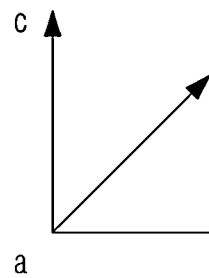

In compression, data is predicted and the difference between the predicted value and the real value are coded. For this reason, a parameter may be adjusted based on the properties of ultrasonic radio frequency (RF) data, and an algorithm may be changed to increase a compression rate. When viewing the property of the ultrasonic diagnostic apparatus 200, therefore, the reflected ultrasound signal forms a temporal redundancy. Referring to FIG. 6, the ultrasound signal includes a plurality of vectors, which are obtained with time delay. RF data obtained with time delay has similar temporal redundancies, which may be used in prediction.

Upon calculation of the prediction error using CALIC, a time-direction variation or a vector-direction variation dp is included as a parameter, and, upon obtaining the predicted pixel value, an algorithm is changed to include de (or dprev). The changed equation is as follows:

$$\hat{I}=GAP(\&dh,\&dv,\&dprev)$$

$$dh=abs(I(w)-I(ww))+abs(I(n)-I(nw))+abs(I(ne)-I(n))$$

$$dv=abs(I(w)-I(nw))+abs(I(n)-I(nn))+abs(I(ne)-I(nne))$$

$$dp=abs(I(w)-I(wp))+abs(I(n)-I(np))+abs(I(ne)-I(nep))$$

Upon obtaining the gradient-adjusted prediction (GAP) from the above equation, a weight factor is applied to dv higher is higher than a weight factor applied to dh, since RF data exhibit higher similarity in the axial direction than in the azimuth direction. Also, a weight factor is applied to dv is higher than a weight factor applied to dh, since RF data has high temporal redundancy.

FIG. 6 shows a horizontal (channel-direction) data variation direction a-b, a vertical (depth-direction) data variation direction a-c, and a vector-direction (time-direction) data variation direction a-d.

As is apparent from the above description, the beamforming operation is performed by the host computer 130 using software rather than hardware, thereby reducing manufacturing costs of the ultrasonic diagnostic apparatus.

Also, an ultrasound signal is compressed and transmitted to the host computer, thereby increasing a transmission rate and thus rapidly performing a post-processing operation on the ultrasound signal.

Although a few exemplary embodiments have been shown and described, it will be appreciated by those skilled in the art that changes may be made in these exemplary embodiments without departing from the principles and spirit of the inventive concept, the scope of which is defined in the claims and their equivalents.

What is claimed is:

1. An ultrasonic diagnostic apparatus comprising:
a probe comprising at least one transducer which transmits an ultrasound signal to a target, receives the ultrasound signal reflected from the target, and transduces the received ultrasound signal into an electrical signal; and
a compressor which compresses the electrical signal by predicting a target pixel of the ultrasound signal from an ambient pixel to generate a prediction error signal and coding the prediction error signal,
wherein the signal compressed by the compressor is decompressed when the signal is used for beamforming.

2. The ultrasonic diagnostic apparatus according to claim 1, wherein the compressor generates the prediction error signal using at least one of channel-direction data and depth-direction of the electrical signal.

3. The ultrasonic diagnostic apparatus according to claim 2, wherein the compressor generates the prediction error signal using the at least one of the channel-direction data and the depth-direction data of the electrical signal by applying weight factors to the at least one of the channel-direction data and the depth-direction to generate a prediction signal and determining a difference between a pixel value of the prediction signal and a pixel value of a real signal, and
wherein the weight factor applied to the depth-direction is higher than the weight factor applied to the channel-direction data.

4. The ultrasonic diagnostic apparatus according to claim 1, wherein the compressor codes the prediction error signal by creating a compressed code word from a sequence of the prediction error signal and coding the compressed code word.

5. The ultrasonic diagnostic apparatus according to claim 1, wherein the compressor removes spatial redundancy, temporal redundancy and statistical redundancy from the electrical signal to compress the electrical signal.

6. The ultrasonic diagnostic apparatus according to claim 1, wherein the signal compressed by the compressor is beamformed so that a frame data signal is created, and
the frame data signal is processed so that an ultrasonic image data is created.

7. The ultrasonic diagnostic apparatus according to claim 6, wherein the ultrasonic image data is converted into image frame data having a scan line display format.

8. The ultrasonic diagnostic apparatus according to claim 7, further comprising a display unit which receives the image frame data from the host computer and displays the image frame data.

9. A method of controlling an ultrasonic diagnostic apparatus, the method comprising:
compressing an ultrasound signal reflected from a target by predicting a target pixel of the ultrasound signal from an ambient pixel to generate a prediction error signal, and coding the prediction error signal;
transmitting the compressed ultrasound signal to a decompressor; and
decompressing the compressed signal and performing beaming forming.

10. The method according to claim 9, wherein the predicting the target pixel of the ultrasound signal from the ambient pixel to generate the prediction error signal comprises generating the prediction error signal based on at least one of a channel-direction variation and a depth-direction variation.

11. The method according to claim 10, wherein the generating the prediction error signal comprises applying weight factors to the at least one of a channel-direction variation and the depth-direction variation to generate a prediction signal and determining a difference between a pixel value of the prediction signal and a pixel value of a real signal, and
wherein the weight factor applied to the depth-direction variation is higher than the weight factor applied to the channel-direction variation.

12. The method according to claim 9, wherein the coding the prediction error signal to perform compression comprises creating a compressed code word from a sequence of the prediction error signal and coding the compressed code word.

13. The method according to claim 9, wherein the compressing the ultrasound signal comprises removing spatial redundancy, temporal redundancy and statistical redundancy from the ultrasound signal.

14. A method of controlling an ultrasonic diagnostic apparatus, the method comprising:
compressing an ultrasound signal reflected from a target;
predicting a target pixel of the ultrasound signal based on an ambient pixel to generate a prediction error signal;
coding the prediction error signal to generate compressed data;
transmitting the compressed data to a decompressor; and
decompressing the compressed data and beamforming using a decompressed data.

15. The method according to claim 14, wherein the predicting the target pixel comprises generating the prediction error signal based on at least one of a channel-direction data and depth-direction.

16. The method according to claim 15, wherein the generating the prediction error signal comprises:
- applying weight factors to the channel-direction data and the depth-direction data; and
- calculating the prediction error signal comprises calculating a difference between a pixel value of the prediction signal and a pixel value of a real signal,
- wherein the weight factor applied to the depth-direction data is higher than the weight factor applied to the channel-direction data.

17. The method according to claim 14, wherein the coding the prediction error signal comprises creating a compressed code word from a sequence of the prediction error signal to code the compressed code word and performing compression.

\* \* \* \* \*